(12) United States Patent
Ikeda et al.

(10) Patent No.: US 9,101,763 B2
(45) Date of Patent: Aug. 11, 2015

(54) PARTICLE BEAM IRRADIATION APPARATUS HAVING ADJUSTABLE LOW-SCATTERING FILLING CHAMBER AND PARTICLE BEAM THERAPY SYSTEM

(75) Inventors: Masahiro Ikeda, Tokyo (JP); Hisashi Harada, Tokyo (JP); Kazushi Hanakawa, Tokyo (JP); Toshihiro Otani, Tokyo (JP); Tadashi Katayose, Tokyo (JP); Taizo Honda, Tokyo (JP); Yukiko Yamada, Tokyo (JP); Yuehu Pu, Tokyo (JP)

(73) Assignee: MITSUBISHI ELECTRIC CORPORATION, Chiyoda-Ku, Tokyo (JP)

( * ) Notice: Subject to any disclaimer, the term of this patent is extended or adjusted under 35 U.S.C. 154(b) by 0 days.

(21) Appl. No.: 14/240,650

(22) PCT Filed: Nov. 3, 2011

(86) PCT No.: PCT/JP2011/075361
§ 371 (c)(1),
(2), (4) Date: Feb. 24, 2014

(87) PCT Pub. No.: WO2013/065163
PCT Pub. Date: May 10, 2013

(65) Prior Publication Data
US 2014/0228615 A1      Aug. 14, 2014

(51) Int. Cl.
*A61N 5/00* (2006.01)
*A61N 5/10* (2006.01)

(52) U.S. Cl.
CPC ............ *A61N 5/1081* (2013.01); *A61N 5/1077* (2013.01); *A61N 2005/1087* (2013.01); *A61N 2005/1095* (2013.01)

(58) Field of Classification Search
CPC .............. A61N 5/1081; A61N 5/1077; A61N 2005/1087; A61N 2005/1095
USPC .................................. 250/492.1, 492.3, 493.1
See application file for complete search history.

(56) References Cited

U.S. PATENT DOCUMENTS

2004/0104354 A1 * 6/2004 Haberer et al. ......... 250/396 ML
2010/0181494 A1 * 7/2010 Mattern ........................ 250/398
(Continued)

FOREIGN PATENT DOCUMENTS

JP       2007-229025 A    9/2007
JP       2010-017365 A    1/2010
(Continued)

OTHER PUBLICATIONS

International Search Report (PCT/ISA/210) mailed on Dec. 13, 2011, by the Japanese Patent Office as the International Searching Authority for International Application No. PCT/JP2011/075361.
(Continued)

*Primary Examiner* — Jack Berman
*Assistant Examiner* — Jason McCormack
(74) *Attorney, Agent, or Firm* — Buchanan Ingersoll & Rooney PC

(57) ABSTRACT

A particle beam irradiation apparatus according to the present invention is provided with a vacuum duct that forms a vacuum region through which the charged particle beam passes, a vacuum window through which the charged particle beam is launched from the vacuum region, a scanning electromagnet that scans the charged particle beam; a monitoring apparatus including a position monitor that detects the passing position of a charged particle beam and the beam size thereof, a low-scattering gas filling chamber including the monitoring apparatus, and an irradiation management apparatus that controls irradiation of the charged particle beam; the particle beam irradiation apparatus is characterized in that the low-scattering gas filling chamber is changeably disposed in such a manner that the beam-axis-direction positional relationship between the monitoring apparatus and the vacuum window is a desired one and in that the low-scattering gas filling chamber is filled with a low-scattering gas.

20 Claims, 13 Drawing Sheets

(56) References Cited

U.S. PATENT DOCUMENTS

| | | | |
|---|---|---|---|
| 2011/0182411 A1* | 7/2011 | Shinagawa et al. | 378/65 |
| 2011/0218429 A1* | 9/2011 | Harada et al. | 600/427 |
| 2012/0316378 A1 | 12/2012 | Torikai et al. | |

FOREIGN PATENT DOCUMENTS

| | | |
|---|---|---|
| JP | 4393581 B1 | 1/2010 |
| JP | 2010-0253240 A | 11/2010 |
| JP | 2011-156340 A | 8/2011 |
| WO | WO 2010/122662 A1 | 10/2010 |
| WO | WO 2010122662 A1 * | 10/2010 |
| WO | WO 2011/080942 A1 | 7/2011 |

OTHER PUBLICATIONS

Office Action issued on Aug. 27, 2014, by the Taiwanese Patent Office in counterpart Taiwanese Patent Application No. 101106937, and an English Translation of the Office Action. (19 pages).

Office Action issued on Jan. 13, 2015, by the Japanese Patent Office in counterpart Japanese Patent Application No. 2013-541554, and an English Translation of the Office Action (8 pages).

* cited by examiner

PARTICLE BEAM IRRADIATION APPARATUS HAVING ADJUSTABLE LOW-SCATTERING FILLING CHAMBER AND PARTICLE BEAM THERAPY SYSTEM

TECHNICAL FIELD

The present invention relates to a particle beam irradiation apparatus and a particle beam therapy system for performing treatment of a cancer or the like by use of a particle beam.

BACKGROUND ART

In general, a particle beam therapy system is provided with a beam generation apparatus that generates a charged particle beam, an accelerator that is connected with the beam generation apparatus and accelerates a generated charged particle beam, a beam transport system that transports a charged particle beam that is accelerated by the accelerator so as to gain predetermined energy and then emitted, and a particle beam irradiation apparatus, disposed at the downstream side of the beam transport system, for irradiating a charged particle beam onto an irradiation subject. Particle beam irradiation apparatuses are roughly divided into apparatuses utilizing a broad irradiation method in which a charged particle beam is enlarged in a dispersion manner by a scatterer, and the shape of the enlarged charged particle beam is made to coincide with the shape of an irradiation subject in order to form an irradiation field; and apparatuses utilizing a scanning irradiation method (the spot-scanning method, the raster-scanning method, and the like) in which an irradiation field is formed by performing scanning with a thin, pencil-like beam in such a way that the scanning area coincides with the shape of an irradiation subject.

In the broad irradiation method, an irradiation field that coincides with the shape of a diseased site is formed by use of a collimator or a bolus. The broad irradiation method is a most universally utilized and superior irradiation method where an irradiation field that coincides with the shape of a diseased site is formed so as to prevent unnecessary irradiation onto a normal tissue. However, it is required to create a bolus for each patient or to change the shape of a collimator in accordance with a diseased site.

In contrast, the scanning irradiation method is a high-flexibility irradiation method where, for example, neither collimator nor bolus is required. However, because these components for preventing irradiation onto not a diseased site but a normal tissue are not utilized, there is required a positional accuracy of beam irradiation that is the same as or higher than that of the broad irradiation method.

In recent years, in order to treat a complex-shape diseased site, the demand for the degree of freedom in forming a beam has become large. It is required to apply the scanning irradiation method to a craniocervical portion, because that portion includes major organs such as the eyeballs, the optic nerve, the spinal cord, the brain, and the like. Unlike a body portion, the size of a craniocervical portion is small; therefore, the depth to a diseased site is relatively small and hence the necessary beam energy is small. FIG. 17 represents the relationship between the energy of a charged particle beam and the beam size thereof. The abscissa denotes the beam energy E (MeV) of a charged particle beam, and the ordinate denotes the beam size S (mm) of the charged particle beam. The beam size is calculated in such a manner as a standard deviation is calculated. In FIG. 17, the beam size S denotes a beam size at an isocenter in water. A characteristic 92 denotes a beam size that is a physical limit caused by water scattering; a characteristic 91 denotes a beam size at a time when a charged particle beam that has been launched through the beam extracting window of a conventional particle beam irradiation apparatus passes through the air and enters the body of a patient. Because the irradiation characteristic of a radiation in a human body is almost the same as that of a radiation in water, an aquatic irradiation characteristic is examined.

For example, the range of a proton beam of 150 MeV is approximately 16 cm when the loss in a beam extracting window, a position monitor, the air, and the like is neglected; in many cases, the range of a craniocervical portion is shorter than the range of the proton beam. In other words, in the case of a conventional technology, even though considering the case, a particle beam having as low energy as 150 MeV and a small size, as represented in FIG. 17, is required, a particle beam of as low energy as 150 MeV is affected largely by scattering (angle) in a beam extracting window, a position monitor, and the air caused before the particle beam enters water; thus, the beam size thereof becomes extremely large. As a method of reducing the beam size, it is conceivable to reduce the distance between a material that scatters a charged particle beam and a to-be-irradiated body (diseased site).

Patent Document 1 discloses an invention in which in a particle beam therapy system utilizing a scanning irradiation method that requires a high accuracy in the beam irradiation position, an obstacle that causes beam scattering is placed at a position that is as downstream in the beam as possible so that the beam size is reduced. The invention disclosed in Patent Document 1 is provided with a beam scanning apparatus that scans a charged particle beam, a first duct in which a beam extracting window is provided at a position that is at the downstream side of the beam scanning apparatus, an irradiation apparatus that makes a charged particle beam pass through the first duct and that irradiates the charged particle beam onto an irradiation subject, a second duct, and a beam transport apparatus that makes a charged particle beam, launched from an accelerator, pass through the second duct and that transports the charged particle beam to the irradiation apparatus; a beam position monitor (referred to simply as a position monitor, hereinafter) that measures the position of a charged particle beam is mounted in the beam extracting window through the intermediary of a holding member; a vacuum region in the first duct and a vacuum region in the second duct communicate with each other.

The first duct includes two ducts; the two ducts are airtightly bonded with each other by use of a bellows. By use of a duct driving means and a duct expansion/contraction means that expands and contracts the first duct in the beam-axis direction, the bellows is expanded and contracted and the position monitor, which is provided at a position that is in the vicinity of and at the downstream side of the beam extracting window, is moved in the beam-axis direction of the duct, so that the air gap between a patient and the beam extracting window is suppressed from becoming unnecessarily large and hence the beam size is reduced.

PRIOR ART REFERENCE

Patent Document

[Patent Document 1] Japanese Patent No. 4393581 (Paragraphs 0014, Paragraphs 0027 through 0029, FIG. 2)

DISCLOSURE OF THE INVENTION

Problem(s) to be Solved by the Invention

In the particle beam therapy system disclosed in Patent Document 1, in order to reduce the distance between the beam extracting window and a patient, there is utilized a bellows that bonds two ducts, included in the first duct, airtightly and in an expandable/contractible manner. As illustrated in FIG. 18, when a vacuum bellows for keeping its inside vacuum is expanded/contracted for a long time as its inside is kept vacuum, its movable range is limited. A bellows 95 shows that a bellows is in a most contracted state; the length of the bellows 95 is L2. A bellows 94 shows that a bellows is in a most expanded state; the length of the bellows 94 is L1. A length L3 is the difference between L1 and L2; the length L3 is a possible stroke length. The possible stroke length L3 is approximately one-third of the maximum length L1; when the stroke length needs to be extended, the overall length of the vacuum bellows becomes longer.

In order to position the diseased site of a patient on a patient platform, the beam-axis-direction traveling length of the patient needs to be the same as or longer than 370 mm. In order to expand or contract the vacuum bellows so as to move the beam extracting window and the position monitor, the possible stroke length L3 needs to be the same as or longer than 370 mm. Considering not only the beam-axis-direction traveling length of a patient but also the positional relationship among the patient, an X-ray tube, and an X-ray image-capturing device, the beam extracting window and the position monitor need to be further away from the patient. In the case where the front end of an irradiation nozzle (the front end of a part thereof at which the position monitor is mounted) is moved to a position where the front end hardly touches the body surface, the position is 40 cm apart from the isocenter; thus, when the maximum retreating length is 650 mm, the possible stroke length needs to be 610 mm. In the scanning irradiation method, because the scanning range of a charged particle becomes wider as the scanning position moves more downstream, it is required to increase the diameter of the vacuum bellows. It is difficult to produce a large-diameter and long vacuum bellows.

In the particle beam therapy system disclosed in Patent Document 1, the vacuum passing length at a time when a charged particle beam passes through a vacuum is made variable so that the size of a beam to be irradiated onto a diseased site becomes as small as possible; however, provision of a vacuum bellows makes the apparatus complex. Moreover, in the case where the possible stroke length cannot sufficiently be extended, it is not made possible to make the beam extracting window and the position monitor sufficiently close to a patient; as a result, with low energy necessary for therapy of a craniocervical portion, the size of a beam to be irradiated onto the patient may not be sufficiently reduced.

The present invention has been implemented in order to solve the foregoing problems; the objective thereof is to obtain a particle beam irradiation apparatus that can irradiate a small-size charged particle beam onto an irradiation subject even when the energy thereof is low.

Means for Solving the Problems

A particle beam irradiation apparatus according to the present invention includes a vacuum duct that forms a vacuum region through which the charged particle beam passes; a vacuum window that includes a nonmetallic window plate, and is provided at the downstream side of the vacuum duct and through which the charged particle beam is launched from the vacuum region; a scanning electromagnet that scans a charged particle beam in a direction that is perpendicular to a beam axis; a monitoring apparatus including a position monitor that detects a passing position of the charged particle beam and a beam size thereof; a low-scattering gas filling chamber that covers the vacuum window and at the downstream side of which, the monitoring apparatus is disposed; and an irradiation management apparatus that controls irradiation of the charged particle beam. The particle beam irradiation apparatus is characterized in that the low-scattering gas filling chamber is changeably disposed in such a manner that the beam axis direction positional relationship between the monitoring apparatus and the vacuum window is a desired one, and in that when the charged particle beam is irradiated, the low-scattering gas filling chamber is filled with a low-scattering gas that scatters the charged particle beam less than air does.

Advantage of the Invention

In a particle beam irradiation apparatus according to the present invention, the low-scattering gas filling chamber is changeably disposed in such a manner that the beam-axis-direction positional relationship between the monitoring apparatus and the vacuum window is a desired one, and the charged particle beam passes through the low-scattering gas filling chamber filled with a low-scattering gas that scatters the charged particle beam less than air does; therefore, it is made possible to irradiate a small-size charged particle beam onto an irradiation subject even when the energy thereof is low.

DESCRIPTION OF REFERENCE NUMERALS

Embodiment 1

Figure 1:
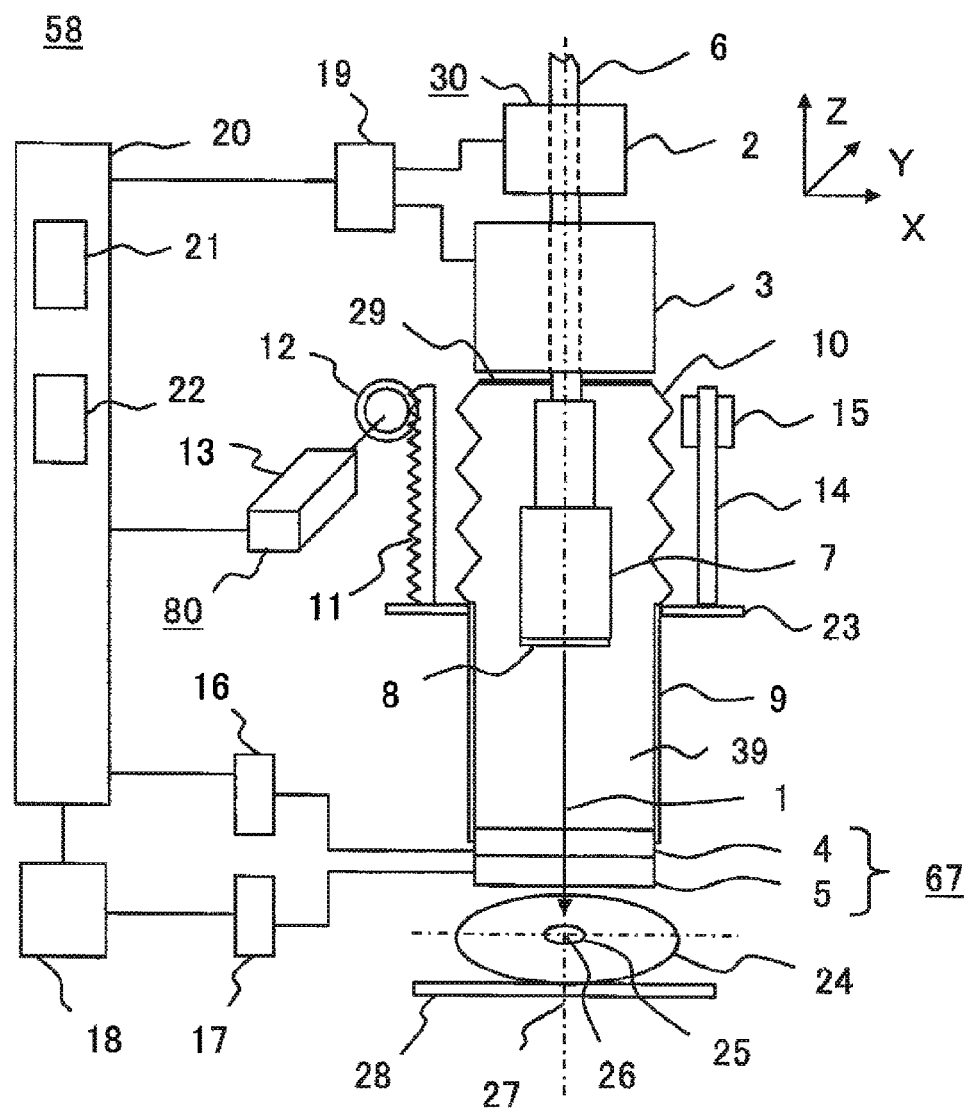
FIG. 1 is a configuration diagram illustrating a particle beam irradiation apparatus according to Embodiment 1 of the present invention.
Figure 2:
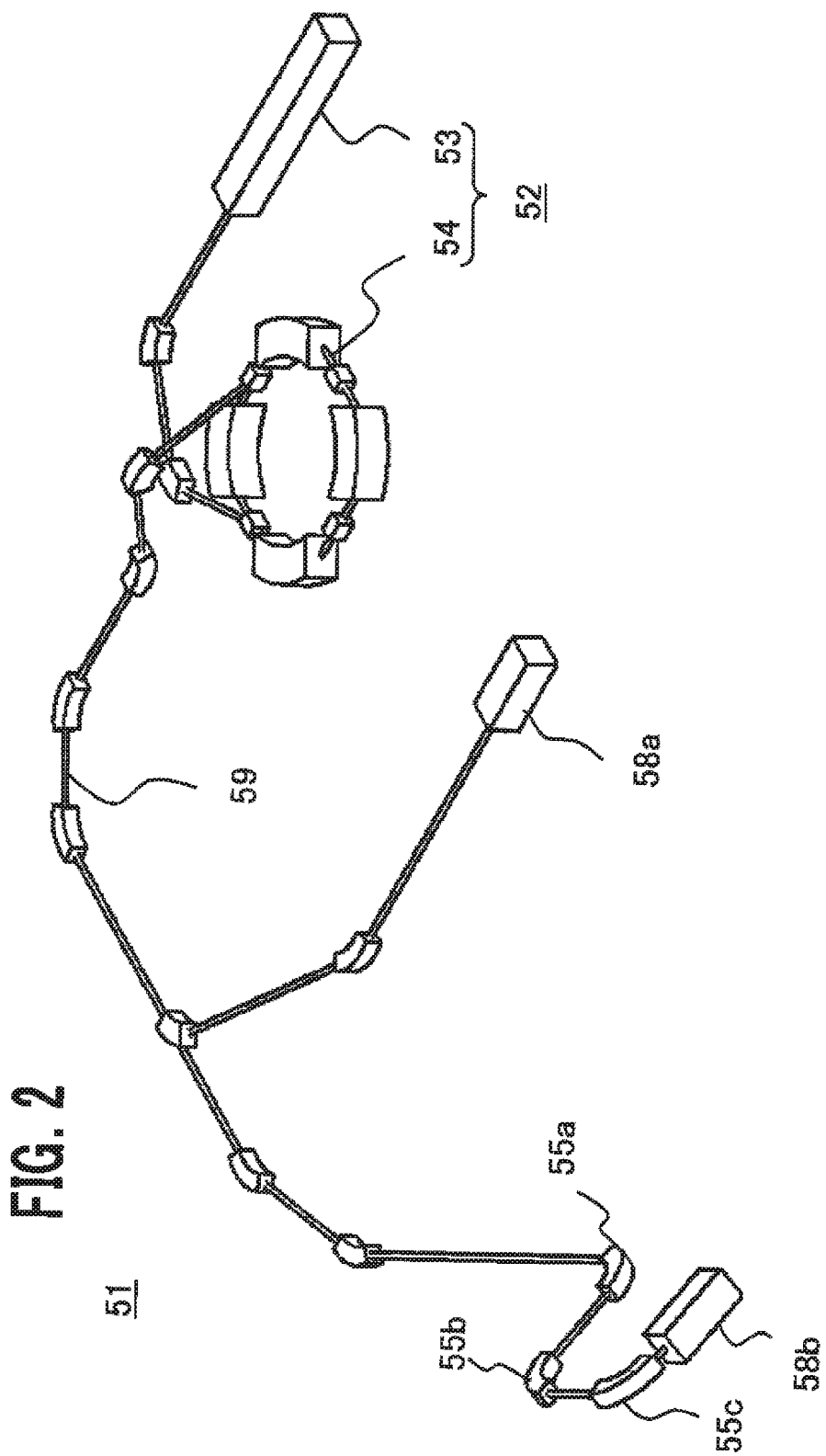
FIG. 2 is a schematic configuration diagram of a particle beam therapy system according to the present invention.

FIG. 1 is a configuration diagram illustrating a particle beam irradiation apparatus according to Embodiment 1 of the present invention. FIG. 2 is a schematic configuration diagram of a particle beam therapy system according to the present invention. In FIG. 2, a particle beam therapy system 51 includes a beam generation apparatus 52, a beam transport system 59, and particle beam irradiation apparatuses 58a and 58b. The beam generation apparatus 52 includes an ion source (unillustrated), a prestage accelerator 53, and a synchrotron 54. The particle beam irradiation apparatus 58b is provided in a rotating gantry (unillustrated). The particle beam irradiation apparatus 58a is provided in a treatment room where no rotating gantry is installed. The function of the beam transport system is to achieve communication between the synchrotron 54 and the particle beam irradiation apparatuses 58a and 58b. Part of the beam transport system 59 is provided in the rotating gantry (unillustrated), and that part includes a plurality of deflection electromagnets 55a, 55b, and 55c.

A charged particle beam, which is a particle beam such as a proton beam generated in the ion source, is accelerated by the prestage accelerator 53 and enters the synchrotron 54, which is an accelerator. The particle beam is accelerated to gain predetermined energy. The charged particle beam launched from the synchrotron 54 is transported to the particle beam irradiation apparatuses 58a and 58b by way of the beam transport system 59. The particle beam irradiation apparatuses 58a and 58b each irradiate the charged particle beam onto an irradiation subject 25 (refer to FIG. 1).

A charged particle beam 1 generated in the beam generation apparatus 52 and accelerated to gain predetermined energy is led to the particle beam irradiation apparatus 58 by way of the beam transport system 59. In FIG. 1, the particle beam irradiation apparatus 58 is provided with an upper vacuum duct 6 and a lower vacuum duct 7 that form a vacuum region from the beam transport system 59 and communicate with each other; a vacuum window 8 through which the charged particle beam 1 is launched from the vacuum region; X-direction and Y-direction scanning electromagnets 2 and 3 that scan the charged particle beam 1 in the X direction and the Y direction, respectively, which are directions perpendicular to the charged particle beam 1; a dose monitor 4; a position monitor 5; an upper seal 29; a monitor holder 9; a bellows 10 that movably connects the upper seal 29 with the monitor holder 9; an extension portion 23 disposed on the outer circumference of the monitor holder 9; a monitor holder driving device 80 that moves the monitor holder 9 in the beam axis; a dose data converter 16; a position data converter 17; a beam data processing apparatus 18; a scanning electromagnet power source 19; and an irradiation management apparatus 20 that controls the particle beam irradiation apparatus 58. The irradiation management apparatus 20 is provided with an irradiation control computer 21 and an irradiation control apparatus 22. The charged particle beam 1 is irradiated along a center axis 27 indicated in FIG. 1; adjustment is performed in such a way that the charged particle beam 1 eventually heads for an isocenter (irradiation reference point) 26 unless the X-direction scanning electromagnet 2 and the Y-direction scanning electromagnet 3 perform any control of the charged particle beam 1. The charged particle beam 1 is irradiated onto a diseased site, i.e., the irradiation subject 25, of a patient 24 mounted on a patient platform 28. The traveling direction of the charged particle beam 1 is −Z direction.

The X-direction and Y-direction scanning electromagnets 2 and 3 scan the charged particle beam 1 in the X direction and the Y direction, respectively. The position monitor 5 detects a beam passing position (gravity center position) and a beam size through which the charged particle beam 1 that has been scanned by the X-direction scanning electromagnet 2 and the Y-direction scanning electromagnet 3 passes. The dose monitor 4 detects the dose of the charged particle beam 1. The irradiation management apparatus 20 controls the irradiation position of the charged particle beam 1 on the irradiation subject 25, based on treatment plan data generated by an unillustrated treatment planning apparatus; when the dose measured by the dose monitor 4 and converted into digital data by the dose data converter 16 reaches a desired dose, the charged particle beam 1 is stopped. The scanning electromagnet power source 19 changes setting currents for the X-direction scanning electromagnet 2 and the Y-direction scanning electromagnet 3, based on control inputs (commands), which are outputted from the irradiation management apparatus 20, to the X-direction scanning electromagnet 2 and the Y-direction scanning electromagnet 3.

The monitor holder driving device 80 is provided with a rack 11 fixed on the extension portion 23, a pinion 12 engaged with the rack 11, a motor 13 that rotates the pinion 12, a guide rail 14 fixed on the extension portion 23, and a guide bush 15 inserted into the guide rail 14. The pinion 12 is fixed at the installation place of the particle beam irradiation apparatus 58 in such a way that the pinion 12, the upper vacuum duct 6, and the lower vacuum duct 7 establish a predetermined positional relationship. The pinion 12 rotated by the motor 13 and the rack 11 that travels in the Z direction through the rotation of the pinion 12 move the monitor holder 9. The dose monitor 4 and the position monitor 5 will collectively be referred to as a monitoring apparatus 67. The monitoring apparatus 67 is fixed on the front end of the monitor holder 9. The method of fixing the monitoring apparatus 67 on the front end of the monitor holder 9 will be described later. The upper seal 29, the bellows 10, the monitor holder 9, and the monitoring apparatus 67 configure a low-scattering gas filling chamber 39. The low-scattering gas filling chamber 39 is filled with a low-scattering gas such as a helium gas. The low-scattering gas filling chamber 39 is changeably disposed in such a manner that the positional relationship, in the beam axis direction, between the monitoring apparatus 67 and the vacuum window 8 is a desired one. The monitor holder driving device 80 is a driving device that changes the positional relationship, in the beam direction (Z direction), between the monitoring apparatus 67 and the vacuum region including the upper vacuum duct 6, the lower vacuum duct 7, and the vacuum window 8 and that changes the volume of the low-scattering gas filling chamber 39 through expansion or contraction of the bellows 10. The upper vacuum duct 6, the lower vacuum duct 7, the vacuum window 8, the low-scattering gas filling chamber 39, the monitoring apparatus 67, the X-direction scanning electromagnet 2, and the Y-direction scanning electromagnet 3 will collectively be referred to as an irradiation-system apparatus 30.

The position monitor 5 is formed, for example, of a multiple-wire proportional counter tube in which a group of vertical wires are stretched in a gas that is ionized by a charged particle. A current signal, which is positional information of a beam on the position monitor 5, is analogue data siga. The analogue data siga is inputted to a position data converter 17. In the position data converter 17, a current signal, which is passing position information of a beam, passes through an I/V converter so as to be converted into a voltage; then, the voltage is amplified by an amplifier and is converted from an analogue signal into a digital signal by an A/D converter. A digital data sigd, obtained through the conversion into a digital signal, is inputted to a beam data processing apparatus 18. The I/V converter, the amplifier, and the A/D converter configure the position data converter 17. The position monitor 4 is formed, for example, of an ionization chamber in which parallel-plate electrodes are provided in air that ionizes a particle beam.

Figure 3:
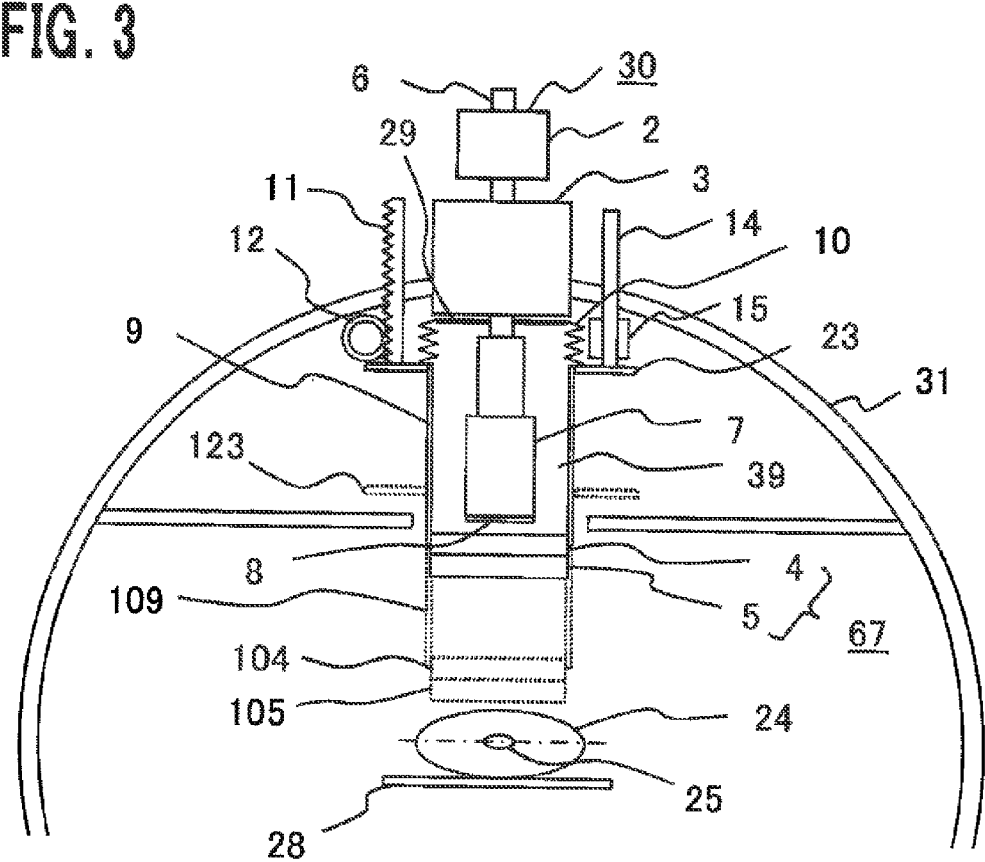
FIG. 3 is a view for explaining a saving mode of an irradiation-system apparatus in FIG. 1.
Figure 4:
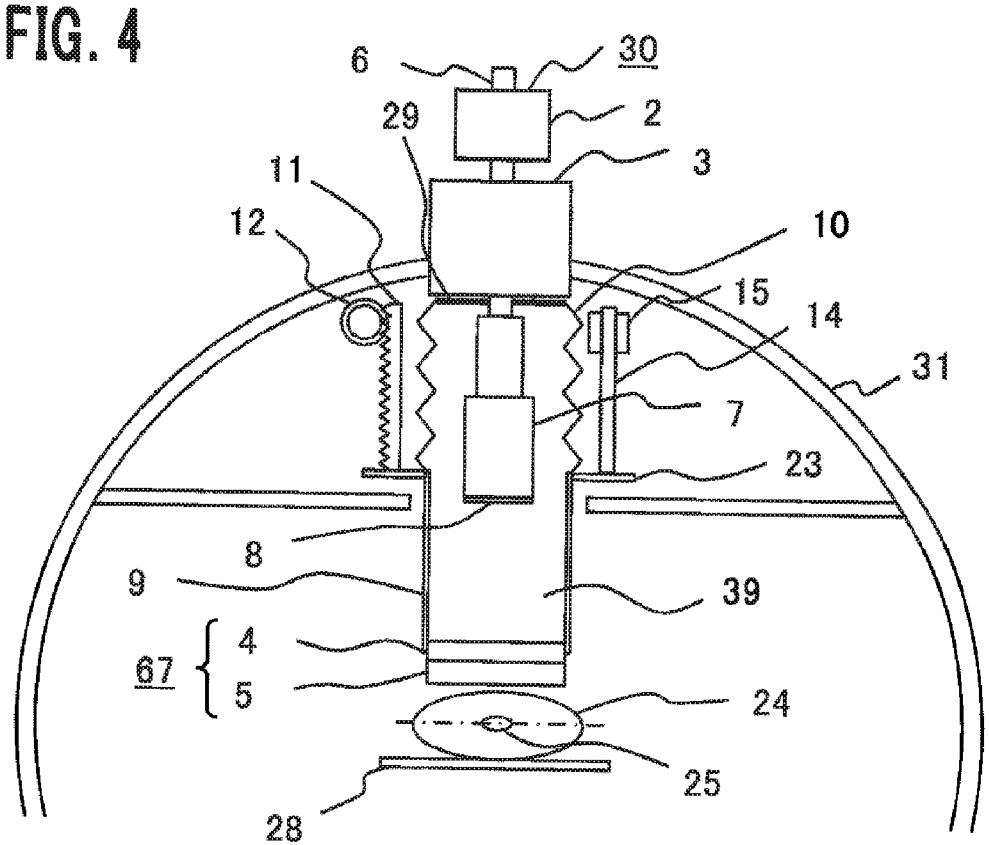
FIG. 4 is a view for explaining an irradiation mode of the irradiation-system apparatuses in FIG. 1.

FIG. 3 is a view for explaining a saving mode of an irradiation-system apparatus; FIG. 4 is a view for explaining an irradiation mode of an irradiation-system apparatus. Each of FIGS. 3 and 4 illustrates an example in which the irradiation-system apparatus 30 is installed in a rotating gantry frame 31. As illustrated in FIG. 3, in the saving mode, the monitoring apparatus 67 approaches the vacuum window 8, so that the monitoring apparatus 67 is moved away from the patient 24. In this saving mode, the patient 24 is mounted on the patient platform 28, and positioning work for the diseased site is implemented. After completion of the positioning work for the diseased site, the monitor holder driving device 80 drives the monitor holder 9 in such a way that the monitoring apparatus 67 approaches the patient 24 as close as possible. The status in which the monitoring apparatus 67 is as close to the patient 24 as possible is illustrated in FIG. 4 and is further indicated by broken lines in FIG. 3. A dose monitor 104 and a position monitor 105 are the dose monitor 4 and the position monitor 5, respectively, at a time when the dose monitor 4 and the position monitor 5 are as close to the patient 24 as possible.

In the particle beam irradiation apparatus 58 according to Embodiment 1, the traveling distance between the monitoring apparatus 67 and the patient 24 can sufficiently be secured with the upper vacuum duct 6, the lower vacuum duct 7, and the vacuum window 8 being left fixed. The low-scattering gas filling chamber 39 is filled with a low-scattering gas that scatters less than air, so that the beam size of the charged particle beam 1 that passes through the low-scattering gas filling chamber 39 can be reduced.

Figure 5:
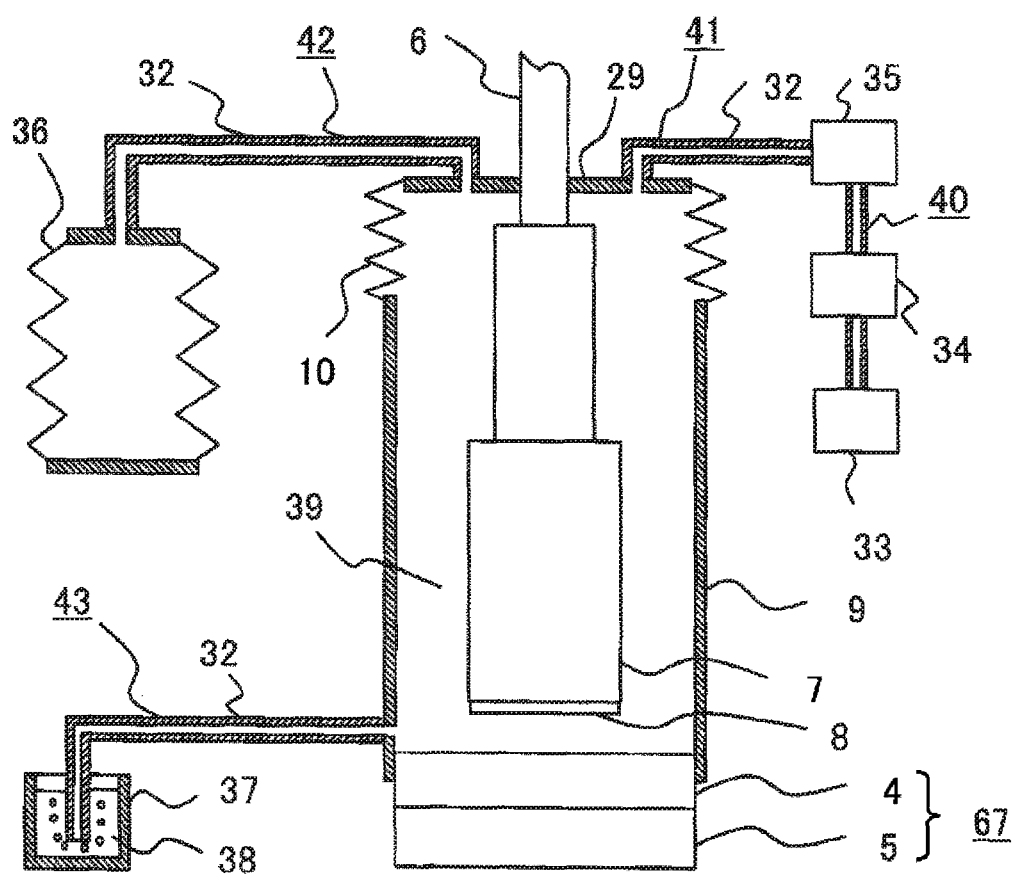
FIG. 5 is a view for explaining a low-scattering gas supply and exhaust configuration according to Embodiment 1.

Next, there will be explained a low-scattering gas supply and exhaust configuration, the structure of the vacuum window 8 in which scattering at a time when a charged particle passes therethrough is small, and the monitoring apparatus 67 equivalent to the cover of the low-scattering gas filling chamber 39. FIG. 5 is a view for explaining a low-scattering gas supply and exhaust configuration according to Embodiment 1. A low-scattering gas apparatus 40 supplies a low-scattering gas to and exhausts the low-scattering gas from the low-scattering gas filling chamber 39. A low-scattering gas apparatus 40 includes a gas supply unit 41, a volume fluctuation absorption unit 42, and a gas exhaust unit 43. The low-scattering gas is supplied from the gas supply unit 41 to the low-scattering gas filling chamber 39. A fluctuation in the pressure of the low-scattering gas in the low-scattering gas filling chamber 39 is adjusted by the volume fluctuation absorption unit 42 and the gas exhaust unit 43 in such a way as to be within a predetermined pressure.

The gas supply unit 41 includes a gas cylinder 33 filled with the low-scattering gas, a regulator 34 for adjusting the pressure of a supplied gas, a flow rate adjustment valve 35 for adjusting the flow rate of the gas supplied to the low-scattering gas filling chamber 39. A pipeline 32 of the gas supply unit 41 is connected, for example, with the upper seal 29. The volume fluctuation absorption unit 42 includes an adjusting chamber 36 and the pipeline 32. In the volume fluctuation absorption unit 42, the low-scattering gas moves from the low-scattering gas filling chamber 39 to the adjusting chamber 36, depending on the gas pressure of the low-scattering gas filling chamber 39. When the gas pressure of the low-scattering gas filling chamber 39 is reduced, the low-scattering gas in the adjusting chamber 36 enters the low-scattering gas filling chamber 39. The volume fluctuation absorption unit 42 changes its volume in accordance with a fluctuation in the gas pressure of the low-scattering gas filling chamber 39 so as to adjust the fluctuation of the low-scattering gas in the low-scattering gas filling chamber 39. The gas exhaust unit 43 includes the pipeline 32 and an oil container 37 containing an oil 38. When the low-scattering gas is supplied to the low-scattering gas filling chamber 39 and the gas pressure of the low-scattering gas filling chamber 39 increases to such an extent as a fluctuation in the gas pressure exceeds the maximum value that can be absorbed by the adjusting chamber 36, the low-scattering gas is exhausted into the oil through the pipeline 32 of the gas exhaust unit 43. The low-scattering gas exhausted into the oil is further exhausted to the outside thereof through an outlet of the oil container 37. The flow rate adjustment valve 35 makes a constant amount of low-scattering gas flow; therefore, a constant amount of low-scattering gas is exhausted through the outlet of the oil container 37.

Figure 6:
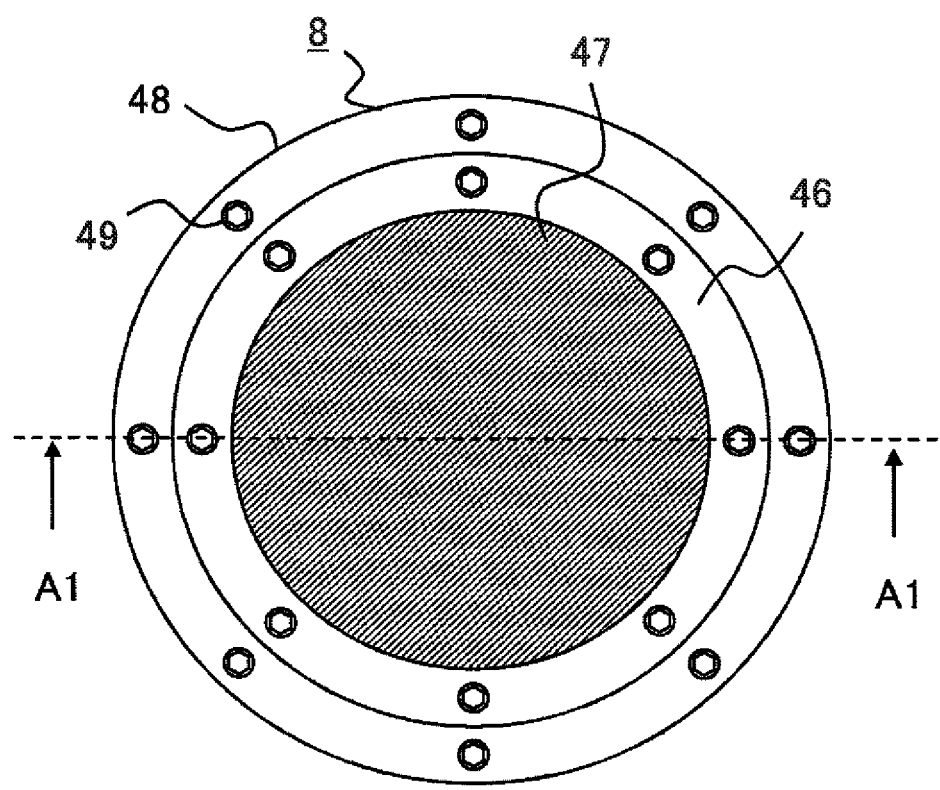
FIG. 6 is a view illustrating the configuration of a vacuum window in FIG. 1.
Figure 7:
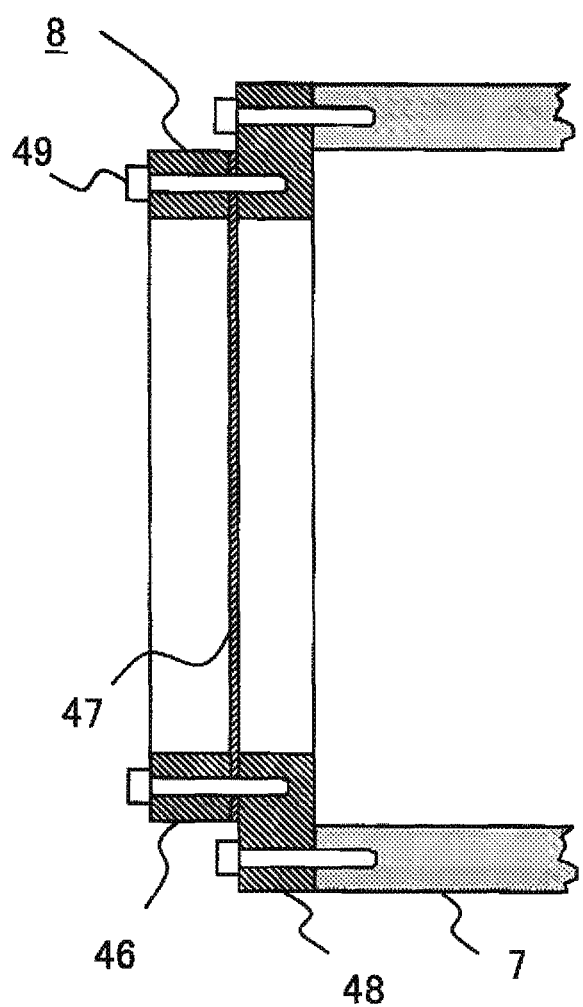
FIG. 7 is a view illustrating the cross section taken along a line A1-A1 in FIG. 6.

FIG. 6 is a view illustrating the configuration of a vacuum window; FIG. 7 is a view illustrating the cross section taken along the line A1-A1 in FIG. 6. On the vacuum window 8, a window plate 47 is pressed and fixed by a mounting flange 48 and a window pressing flange 46. The vacuum window 8 illustrated in each of FIGS. 6 and 7 is an example of circular vacuum window. The window plate 47 is a polyimide plate having a thickness of, for example, 200 μm. Through-holes are formed in the mounting flange 48 made of metal and the window pressing flange 46 made of metal. The window plate 47 is disposed in such a way as to cover the through-holes in the mounting flange 48. The window pressing flange 46 is disposed in such a way as to overlap with the outer circumference of the window plate 47 and is fixed on the mounting flange 48 with bolts 49. The bolts 49 fix the vacuum window 8 on the lower vacuum duct 7 made of metal. The foregoing vacuum window 8 makes it possible to secure a necessary vacuum level of the vacuum region and to suppress the window plate 47 as much as possible from scattering the charged particle beam 1.

Figure 8:
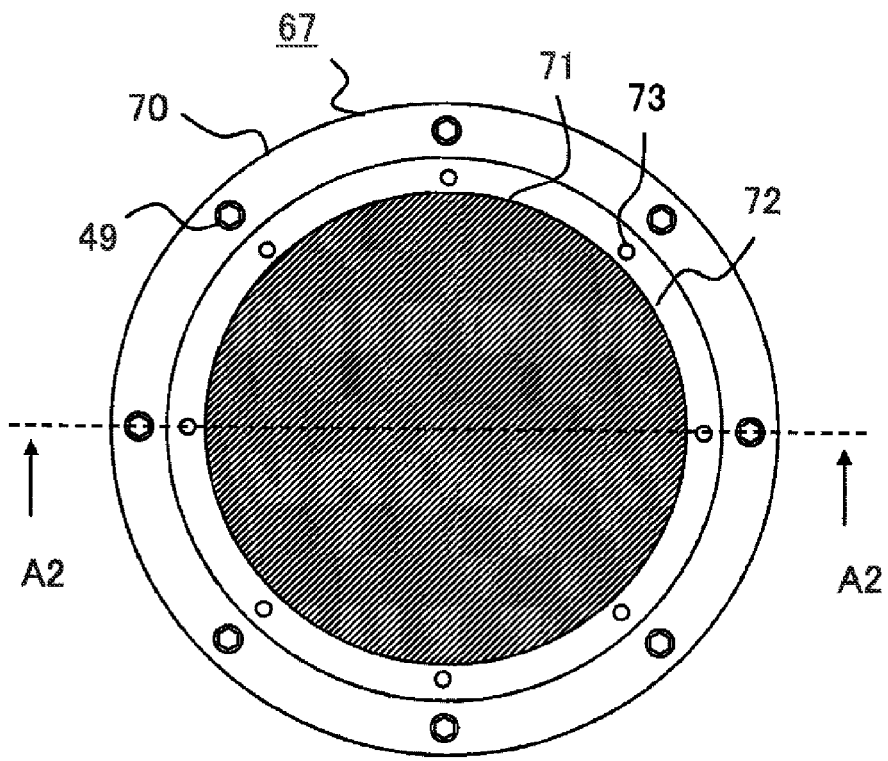
FIG. 8 is a view illustrating a monitoring apparatus in FIG. 1.
Figure 9:
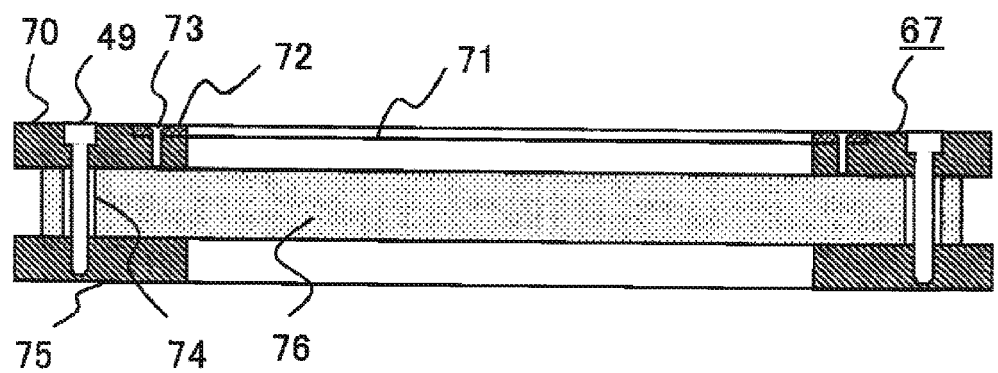
FIG. 9 is a view illustrating the cross section taken along a line A2-A2 in FIG. 8.
Figure 10:
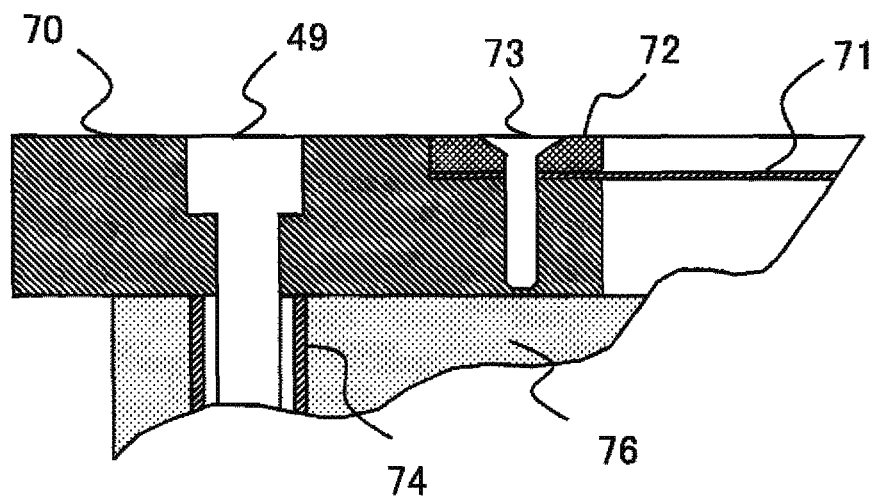
FIG. 10 is an enlarged view of the top-left portion of FIG. 9.

FIG. 8 is a view illustrating a monitoring apparatus. FIG. 9 is a view illustrating the cross section taken along the line A2-A2 in FIG. 8. FIG. 10 is an enlarged view of the top-left portion of FIG. 9. The monitoring apparatus 67 illustrated in each of FIGS. 8 through 10 is an example of circular monitoring apparatus. The monitoring apparatus 67 illustrated in each of FIGS. 8 through 10 is an example in which a monitor electrode portion 76 where the electrode portion of the dose monitor 4 and the electrode portion of the position monitor 5 are arranged in such a way as to overlap with each other is disposed between an upper frame 70 having through-holes and a lower frame 75 having through-holes. For example, eight insulation collars 74 are arranged at the outer circumference side of the monitor electrode portion 76. The bolt 49 is inserted into the bolt hole of the upper frame 70 and the through-hole of the insulation collar 74 and then is screwed into the female screw portion of the lower frame 75, so that the upper frame 70, the lower frame 75, and the monitor electrode portion 76 are integrated.

A window plate 71 is fixed on the upper frame 70 that is disposed at the inner face side of the low-scattering gas filling chamber 39. The window plate 71 is disposed in such a way as to cover the through-hole of the upper frame 70. A window plate pressing frame 72 is disposed in such a way as to overlap with the outer circumference of the window plate 71, and the window plate 71 and the window plate pressing frame 72 are fixed with a screw 73 at the inner circumference side of the upper frame 70. The window plate 71 is a thin mica plate (Mylar film) having a thickness of, for example, 100 µm. The window plate 71 is disposed on the inner-side face of the low-scattering gas filling chamber 39 so as to prevent the low-scattering gas from going downstream therethrough.

Figure 11:
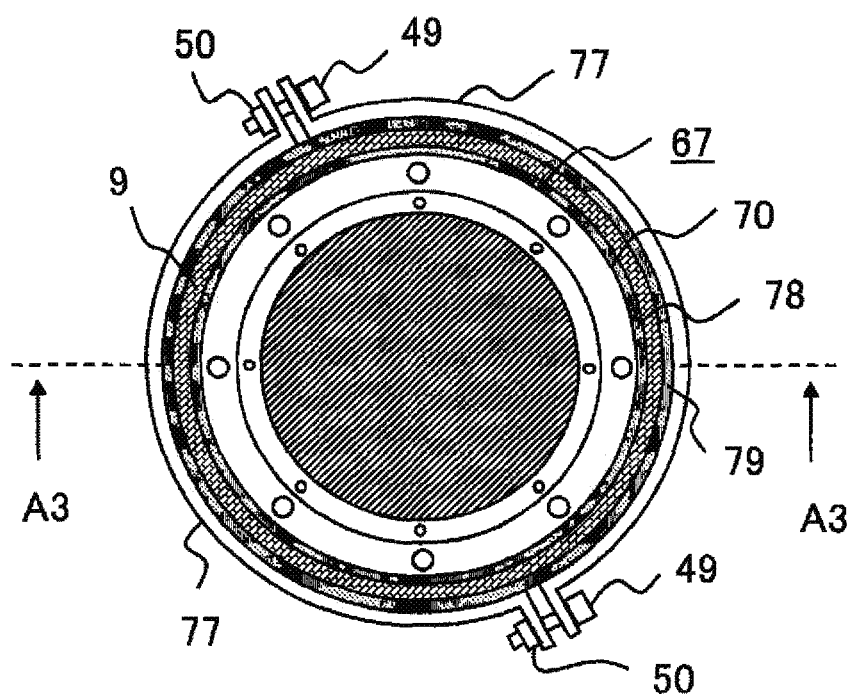
FIG. 11 is a view for explaining a method of mounting the monitoring apparatus in FIG. 1.
Figure 12:
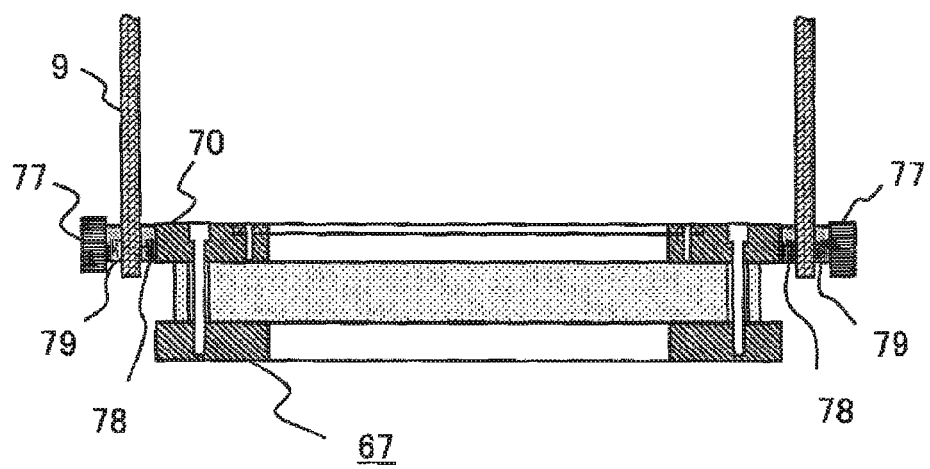
FIG. 12 is a view illustrating the cross section taken along a line A3-A3 in FIG. 11.

The method of connecting the monitor holder 9 with the monitoring apparatus 67 will be explained. FIG. 11 is a view for explaining the mounting method for the monitoring apparatus; FIG. 12 is a view illustrating the cross section taken along the line A3-A3 in FIG. 11. FIG. 11 is a view of the monitoring apparatus 67 when viewed in the irradiation direction of the charged particle beam 1, i.e., in the direction from the upstream side to the downstream side. A seal material 78, the monitor holder 9, the seal material 79, and a pressing device 77 are arranged at the outer circumference side of the upper frame of the monitoring apparatus 67. Two end portions of a pressing device 77 are tightened with the bolt 49 and a nut 50 so that the monitor holder 9 is pressed against and connected with the monitoring apparatus 67; therefore, the airtightness in the connection between the monitor holder 9 and the monitoring apparatus 67 can be secured. Because the airtightness in the connection between the monitor holder 9 and the monitoring apparatus 67 is high, the low-scattering gas filling chamber 39 configured with the upper seal 29, the bellows 10, the monitor holder 9, and the monitoring apparatus 67 can have an airtightness enough to fill a low-scattering gas therein.

Figure 13:
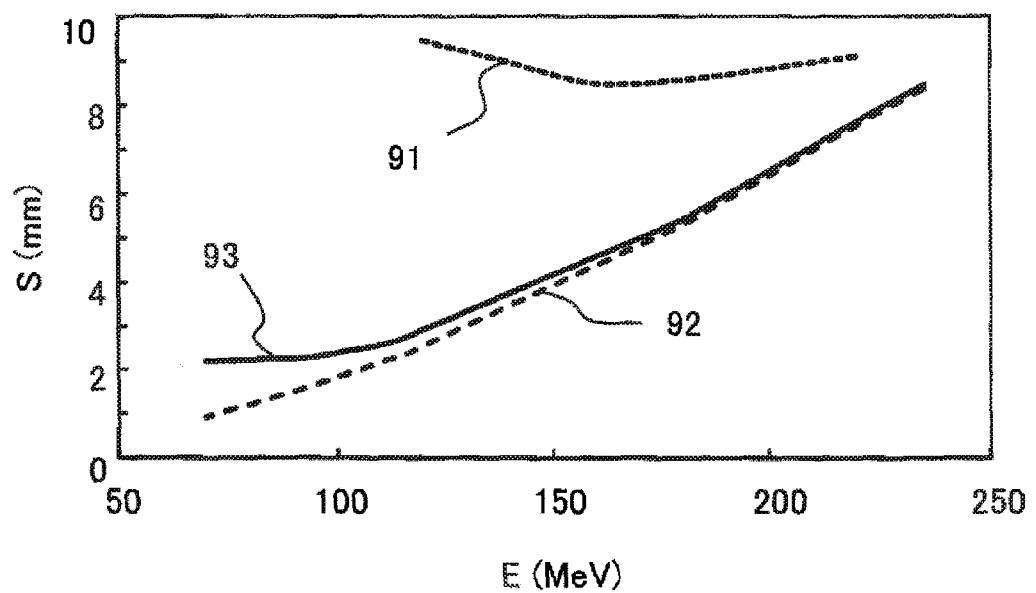
FIG. 13 is a graph representing a beam size characteristic according to the present invention.

FIG. 13 is a graph representing a beam size characteristic according to the present invention. The abscissa denotes the beam energy E (MeV) of a charged particle beam, and the ordinate denotes the beam size S (mm) of the charged particle beam. The beam size S is calculated in such a manner as a standard deviation is calculated. In FIG. 13, the beam size S denotes a beam size at an isocenter in water. A characteristic 93 is the one at a time when as the low-scattering gas, a helium (He) gas is utilized and the low-scattering gas filling chamber 39 is filled with the helium gas. The characteristic in FIG. 13 is an example in which the distance between the vacuum window 8 and the isocenter 26 is 770 mm, the distance between the upper face of the monitoring apparatus 67 and the water surface is 110 mm, and the thickness of the window plate 47 of the vacuum window 8 is 200 µm. When the Bragg peak position in the water is changed by changing the energy of the charged particle beam 1, the water surface and the monitoring apparatus 67 are moved in such a way that the distance between the vacuum window 8 and the isocenter 26 becomes 770 mm and the distance between the upper face of the monitoring apparatus 67 and the water surface becomes 110 mm. When the energy of the charged particle beam 1 is changed, the Z-axis-direction length of the low-scattering gas filling chamber 39 changes. For the sake of comparison, characteristics 91 and 92 are added. The characteristic 92 denotes a beam size that is a physical limit caused by water scattering; the characteristic 91 denotes a beam size at a time when a charged particle beam that has been launched through the beam extracting window of a conventional particle beam irradiation apparatus passes through the air and enters the body of a patient.

The low-scattering gas filling chamber 39 is filled with a helium gas and the distance between the upper face of the monitoring apparatus 67 and the water surface is made to be 110 mm, so that it is made possible to make the beam size close to a beam size that is a physical limit caused by water scattering, when the beam energy is between 70 MeV and 235 MeV. The beam size in the characteristic 93 according to the present invention can be made much smaller than the beam size in the characteristic 91 for a conventional beam size, when the beam energy is between 70 MeV and 235 MeV. In a low-energy range (the same as or lower than 150 MeV) in which a conventional beam size becomes large, the beam size in the characteristic 93 according to the present invention, unlike the beam size in the conventional characteristic 91, can be made small even when the beam energy is lowered. Even though the beam size in the characteristic 93 according to the present invention cannot be made smaller even when the beam energy is lowered to approximately 70 MeV, it is made possible to obtain a beam size that is conspicuously small in comparison with a beam size according to a conventional characteristic. The beam size in the characteristic 93 according to the present invention can be made close to the beam size in the physical-limit characteristic 92, when the beam energy is between 70 MeV and 235 MeV.

In the particle beam irradiation apparatus 58 according to Embodiment 1, the vacuum passing length with which the charged particle beam 1 passes through a vacuum is fixed, the vacuum window 8 is covered, the low-scattering gas filling chamber 39 filled with a low-scattering gas is provided, and the monitoring apparatus 67 situated at the front end portion of the low-scattering gas filling chamber 39 is made as close to a patient as possible; therefore, even when the energy of the charged particle beam 1 is low, the charged particle beam 1 having a small beam size can be irradiated onto the irradiation subject 25. Moreover, because in the particle beam irradiation apparatus 58, the vacuum passing length which the charged particle beam 1 passes through a vacuum is fixed, it is not required, unlike a conventional apparatus, to make the vacuum passing length variable by use of a vacuum bellows; therefore, the configuration of the irradiation-system apparatus 30 can be simplified. Because the configuration of the irradiation-system apparatus 30 is simple, it is made possible that the designing of the traveling distance of the monitoring apparatus 67, i.e., the traveling distance of the monitor holder 9 is freely implemented without being affected by limiting conditions on the vacuum bellows.

As far as the low-scattering gas filling chamber 39 is concerned, it is only necessary to fill it with a low-scattering gas; therefore, it is not required to set such an airtightness as the inside thereof is made vacuum and hence it may be allowed that the low-scattering gas filling chamber 39 is formed of a resin material such as plastic. It may also be allowed that the bellows 10 is formed of a resin material such as plastic or a cloth painted with resin.

Because as the monitoring apparatus 67, the dose monitor 4 and the position monitor 5 are integrated with each other, the beam-irradiation-direction (Z-direction) length of the monitoring apparatus 67 can be reduced in comparison with the case where the dose monitor 4 and the position monitor 5 are superimposed on each other. Because the beam-irradiation-direction (Z-direction) length of the monitoring apparatus 67 in which the dose monitor 4 and the position monitor 5 are integrated with each other is small, its weight can be reduced and hence it is made possible to make the cause agent that scatters the charged particle beam 1 as thin as possible.

As described above, the particle beam irradiation apparatus 58 according to Embodiment 1 is provided with the vacuum ducts 6 and 7 that form a vacuum region through which the charged particle beam 1 passes; the vacuum window 8 that is provided at the downstream side of the vacuum ducts 6 and 7 and through which the charged particle beam 1 is launched from the vacuum region; the scanning electromagnets 2 and 3 that each scan the charged particle beam 1 in a direction that is perpendicular to the beam axis; the monitoring apparatus 67 including the position monitor 5 that detects the passing position of a charged particle beam 1 and the beam size thereof; the low-scattering gas filling chamber 39 that covers the vacuum window 8 and at the downstream side of which, the monitoring apparatus 67 is disposed; and the irradiation management apparatus 20 that controls irradiation of the charged particle beam 1. The low-scattering gas filling chamber 39 is changeably disposed in such a manner that the beam axis direction positional relationship between the monitoring apparatus 67 and the vacuum window 8 is a desired one, and when the charged particle beam 1 is irradiated, the low-scattering gas filling chamber 39 is filled with a low-scattering gas that scatters the charged particle beam 1 less than air does. As a result, the low-scattering gas filling chamber 39 is changeably disposed in such a manner that the beam axis direction positional relationship between the monitoring apparatus 67 and the vacuum window 8 is a desired one, and the charged particle beam 1 can passes through the low-scattering gas filling chamber 39 filled with a low-scattering gas that scatters the charged particle beam 1 less than air does; therefore, even when its energy is low, the charged particle beam 1 having a small beam size can be irradiated onto the irradiation subject 25.

A particle beam therapy system according to Embodiment 1 is provided with the beam generation apparatus 52 that generates the charged particle beam 1 and accelerates it by means of the accelerator 54, the beam transport system 59 that transports the charged particle beam 1 accelerated by the accelerator 54, and the particle beam irradiation apparatus 58 that irradiates the charged particle beam 1 transported by the beam transport system onto the irradiation subject 25; the particle beam irradiation apparatus 58 is provided with the vacuum ducts 6 and 7 that form a vacuum region through which the charged particle beam 1 passes, the vacuum window 8 that is provided at the downstream side of the vacuum ducts 6 and 7 and through which the charged particle beam 1 is launched from the vacuum region, the scanning electromagnets 2 and 3 that each scan the charged particle beam 1 in a direction that is perpendicular to the beam axis, the monitoring apparatus 67 including the position monitor that detects the passing position of a charged particle beam 1 and the beam size thereof, the low-scattering gas filling chamber 39 that covers the vacuum window 8 and at the downstream side of which, the monitoring apparatus 67 is disposed, and the irradiation management apparatus 20 that controls irradiation of the charged particle beam 1. The low-scattering gas filling chamber 39 is changeably disposed in such a manner that the beam axis direction positional relationship between the monitoring apparatus 67 and the vacuum window 8 is a desired one, and when the charged particle beam 1 is irradiated, the low-scattering gas filling chamber 39 is filled with a low-scattering gas that scatters the charged particle beam 1 less than air does. As a result, the low-scattering gas filling chamber 39 is changeably disposed in such a manner that the beam axis direction positional relationship between the monitoring apparatus 67 and the vacuum window 8 is a desired one, and the charged particle beam 1 can passes through the low-scattering gas filling chamber filled with a low-scattering gas that scatters the charged particle beam 1 less than air does; therefore, even when its energy is low, the charged particle beam 1 having a small beam size can be irradiated onto the irradiation subject 25.

Embodiment 2

In Embodiment 1, as the low-scattering gas exhaust configuration in the low-scattering gas filling chamber 39, there has been explained an example, i.e., the gas exhaust unit 43 including the pipeline 32 and the oil container 37 containing the oil 38. In Embodiment 2, there will be explained an example in which a low-scattering gas is exhausted from the gas exhaust unit 43 to the patient side of the monitoring apparatus 67.

Figure 14:
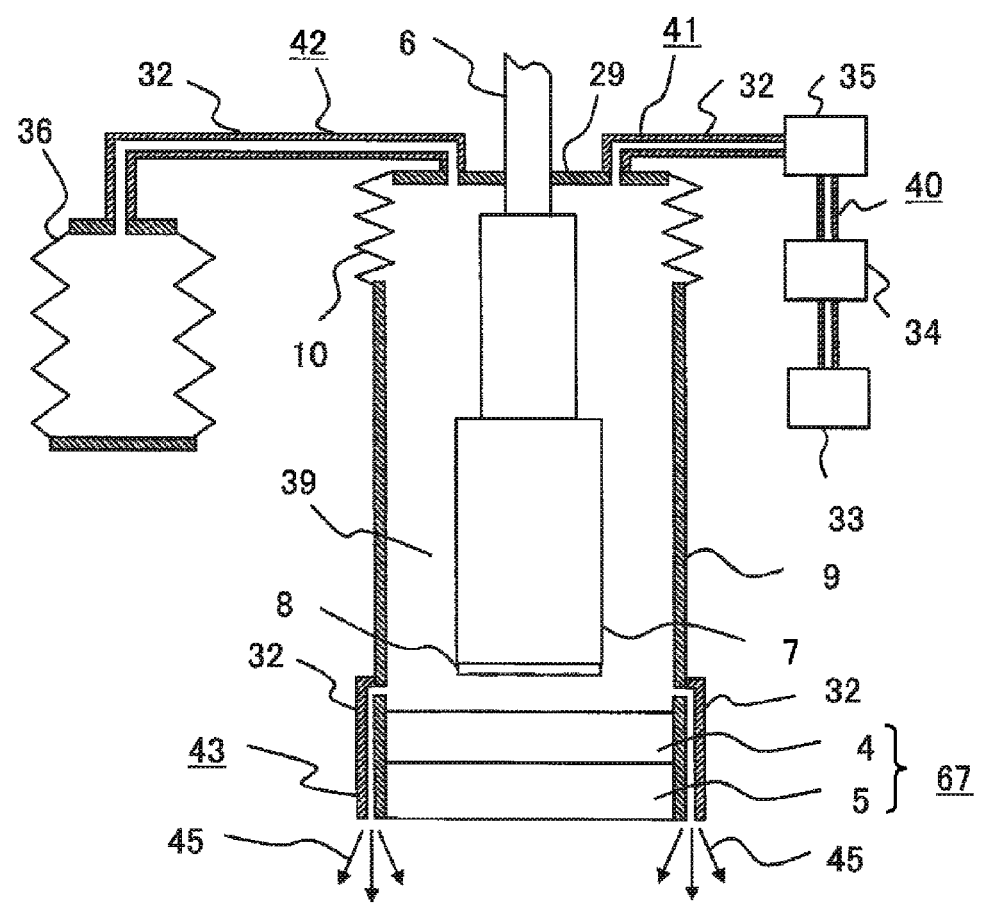
FIG. 14 is a view for explaining a low-scattering gas supply and exhaust configuration according to Embodiment 2.

FIG. 14 is a view for explaining a low-scattering gas supply and exhaust configuration according to Embodiment 2. The gas exhaust unit in Embodiment 2 is different from the gas exhaust unit 43 in FIG. 5 in that the oil container 37 containing the oil 38 is not provided and the pipeline 32 is disposed along the beam-irradiation direction (Z direction) of the monitoring apparatus 67 so that the low-scattering gas in the low-scattering gas filling chamber 39 is made to flow to the patient side of the monitoring apparatus 67. The low-scattering-gas exhaust gas 45 is exhausted from the front end portion of the pipeline 32 toward a patient. Because the exhausted low-scattering gas flows into the space between the monitoring apparatus 67 and the patient 24, the concentration of the low-scattering gas is raised in comparison with the case where the space between the monitoring apparatus 67 and the patient 24 is filled with air; therefore, there can be reduced the scattering in which the beam size of the charged particle beam 1 increases in the space between the monitoring apparatus and the patient 24. Accordingly, the beam size in the particle beam irradiation apparatus 58 according to Embodiment 2 can be made smaller than the beam size in Embodiment 1.

Embodiment 3

Figure 15:
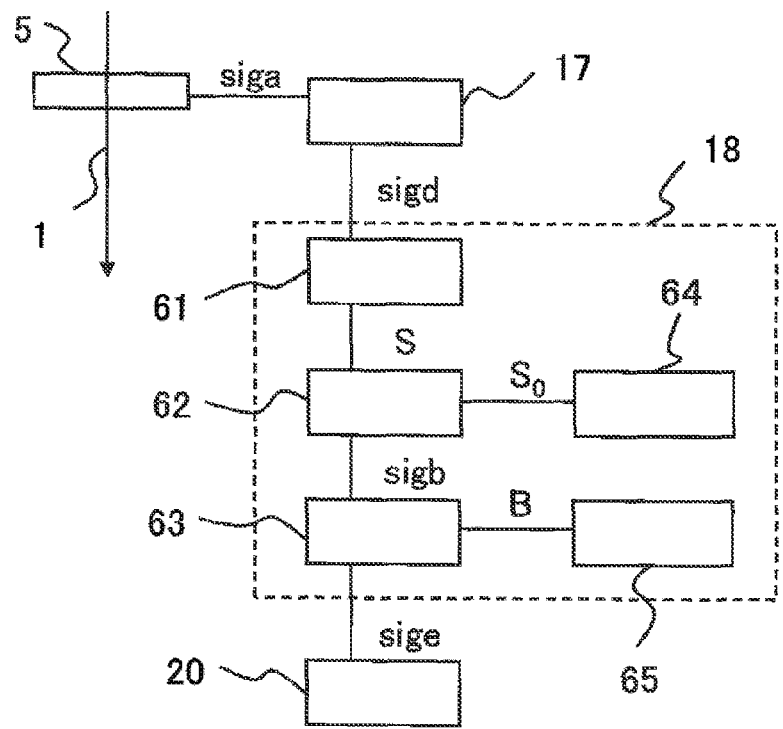
FIG. 15 is a diagram for explaining beam size abnormality determination processing according to Embodiment 3.

In Embodiment 3, there will be explained an example of the particle beam irradiation apparatus 58 having a function of detecting an abnormality in the low-scattering gas filling chamber 39 when an abnormality is caused in the concentration of a low-scattering gas filling chamber 39. When an abnormality is caused in the low-scattering gas filling chamber 39, the concentration of the low-scattering gas in the low-scattering gas filling chamber 39 decreases and hence the beam size of the charged particle beam 1 increases; thus, by utilizing this phenomenon, the abnormality in the low-scattering gas filling chamber 39 is detected. FIG. 15 is a diagram for explaining beam size abnormality determination processing according to Embodiment 3. The beam size abnormality determination processing is performed by the beam data processing apparatus 18. The beam data processing apparatus 18 determines the beam size, based on passing position information of the charged particle beam 1 detected by the position monitor 5.

The beam data processing device 18 is provided with a beam size calculation unit 61 that calculates the beam size S, a beam size storage device 64 that stores a planned desired beam size $S_0$ of the charged particle beam 1 to be irradiated onto the irradiation subject 25, a determination threshold value storage device 65 that stores a determination threshold value B for the abnormality determination with regard to the desired beam size $S_0$, a comparison unit 62 that compares the beam size S with the desired beam size $S_0$ and outputs a size difference sigb between the beam size S and the desired beam size $S_o$, and an abnormality determination unit 63 that determines whether or not the size difference sigb is within the determination threshold value B.

When the abnormality determination unit 63 detects an abnormality in the beam size S, i.e., in the case where the size difference sigb is not within the determination threshold value B, the beam data processing apparatus 18 transmits an abnormality notification signal sige to the irradiation management apparatus 20. When receiving the abnormality notification signal sige, the irradiation management apparatus performs, for example, interlock processing, which is emergency stop processing, so as to stop irradiation of the charged particle beam 1.

As described above, when an abnormality is caused in the low-scattering gas filling chamber 39, the particle beam irradiation apparatus 58 detects an abnormality in the beam size S of the charged particle beam 1 and then performs interlock processing, which is emergency stop processing; thus, irradiation of the charged particle beam 1 can be stopped.

An example has been explained in which the irradiation management apparatus 20 receives the abnormality notification signal sige from the beam data processing apparatus 18 and then performs interlock processing, which is emergency stop processing; however, it may be allowed that the beam data processing apparatus 18 transmits abnormality notification signals sige corresponding to a plurality of abnormality levels and in accordance with the level of the abnormality notification signal sige, the irradiation management apparatus 20 adjusts the gas supply amount of the gas supply unit 41.

Figure 16:
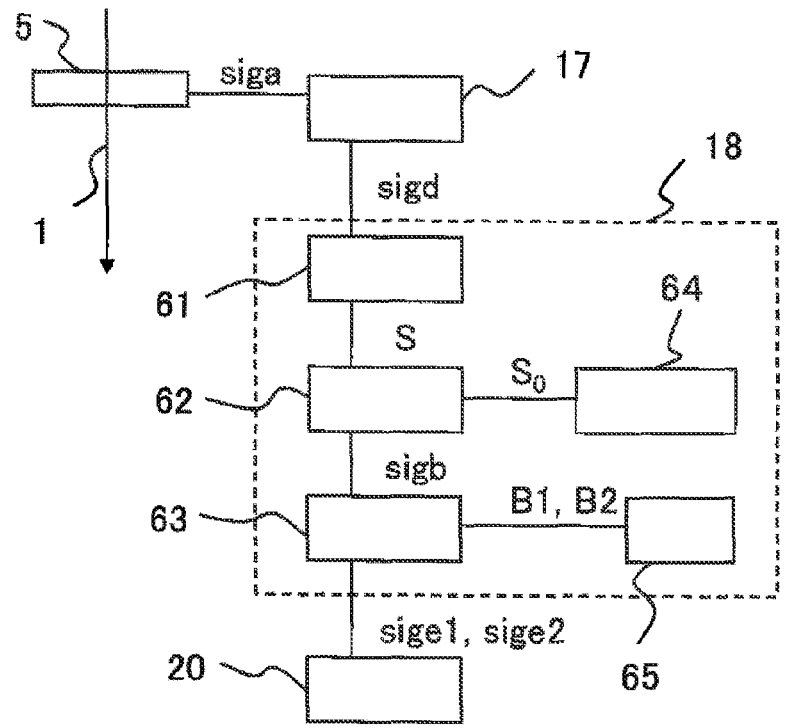
FIG. 16 is a diagram for explaining another beam size abnormality determination processing according to Embodiment 3.
Figure 17:
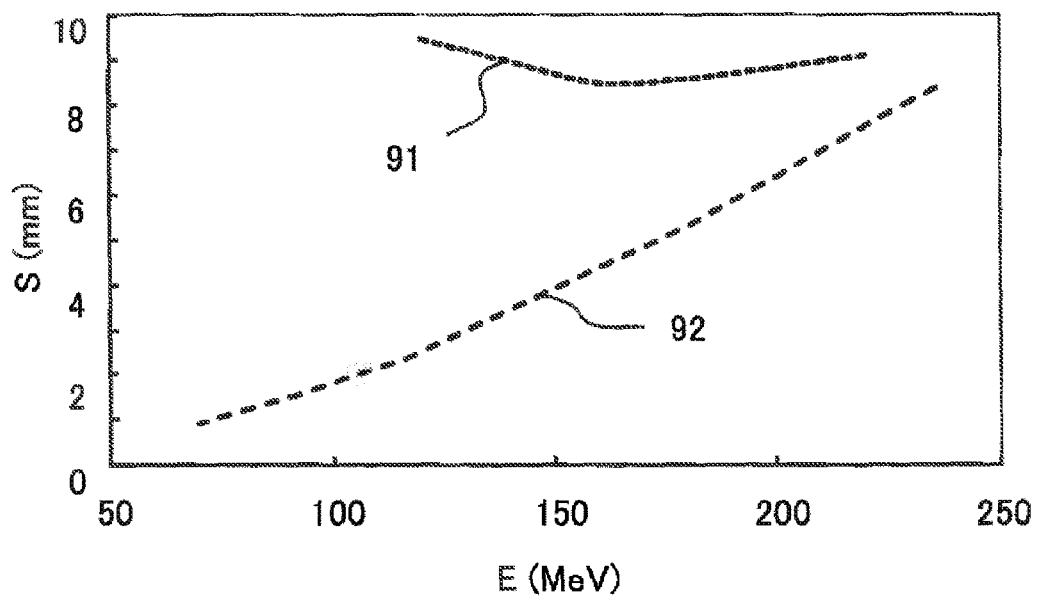
FIG. 17 is a graph for explaining the relationship between the energy of a charged particle beam and the beam size thereof.
Figure 18:
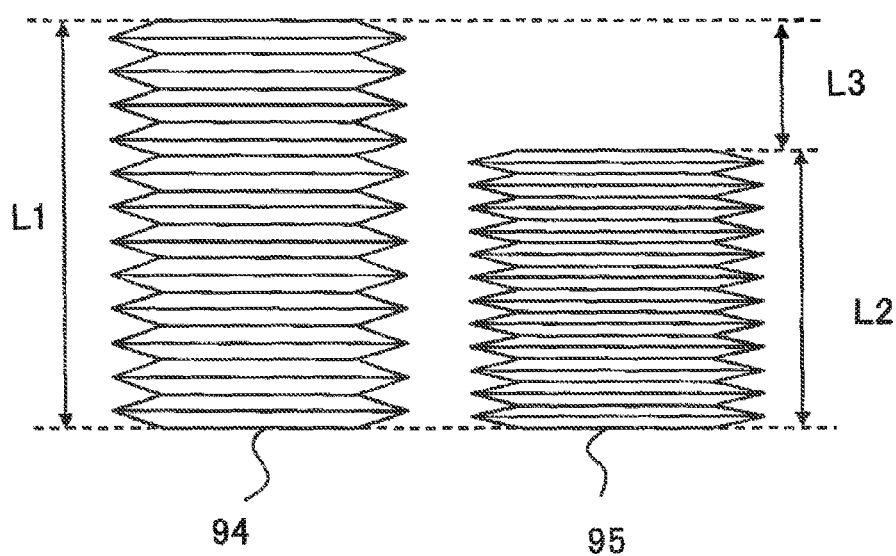
FIG. 18 is a view for explaining a problem in a vacuum bellows.

For example, the case where the beam data processing apparatus 18 generates two abnormality notification signals sige1 and sige2 will be explained. FIG. 16 is a diagram for explaining another beam size abnormality determination processing according to Embodiment 3. In this case, two threshold values B1 and B2 are stored in the determination threshold value storage device 65. In this situation, it is assumed that B1 is smaller than B2. In the case where the size difference sigb is not within the range of the determination threshold value B2, the abnormality determination unit 63 transmits the abnormality notification signal sige2 to the irradiation management apparatus 20. In the case where the size difference sigb is within the range of the determination threshold value B2 but not within the range of the determination threshold value B1, the abnormality determination unit 63 transmits the abnormality notification signal sige1 to the irradiation management apparatus 20. When receiving the abnormality notification signal sige2, the irradiation management apparatus 20 performs interlock processing, which is emergency stop processing, so as to stop irradiation of the charged particle beam 1. When receiving the abnormality notification signal sige1, the irradiation management apparatus 20 transmits a control signal to the gas supply unit 41 so as to adjust the gas supply amount of the gas supply unit 41.

In the case where the level of the abnormality notification signal sige is set in a further fine manner, the gas supply amount of the gas supply unit 41 can finely be adjusted.

Heretofore, the example where no vacuum bellows is utilized has been explained; however, it may be allowed that a vacuum bellows that makes a short-distance moving possible and a low-scattering gas filling chamber are concurrently utilized.

DESCRIPTION OF REFERENCE NUMERALS

1: charged particle beam
2: X-direction scanning electromagnet
3: Y-direction scanning electromagnet
5: position monitor
6: upper vacuum duct
7: lower vacuum duct
8: vacuum window
9: monitor holder
10: bellows
18: beam data processing apparatus
20: irradiation management apparatus
25: irradiation subject
29: upper seal
32: pipeline
37: oil container
38: oil
39: low-scattering gas filling chamber
40: low-scattering gas apparatus
41: gas supply unit
42: volume fluctuation absorption unit
43: gas exhaust unit
61: beam size calculation unit
63: abnormality determination unit
67: monitoring apparatus
71: window plate
51: particle beam therapy system
52: beam generation apparatus
54: synchrotron (accelerator)
58, 58a, 58b: particle beam irradiation apparatus
59: beam transport system
sige, sige1, sige2: abnormality notification signal
S: beam size
$S_0$: desired beam size
B, B1, B2: determination threshold value

The invention claimed is:

1. A particle beam irradiation apparatus that irradiates a charged particle beam accelerated by an accelerator onto an irradiation subject, the particle beam irradiation apparatus comprising:
a vacuum duct that forms a vacuum region through which the charged particle beam passes;
a vacuum window that includes a nonmetallic window plate, and is provided at the downstream side of the vacuum duct and through which the charged particle beam is launched from the vacuum region;
a scanning electromagnet that scans the charged particle beam in a direction that is perpendicular to a beam axis;
a monitoring apparatus including a position monitor that detects a passing position of the charged particle beam and a beam size thereof;
a low-scattering gas filling chamber that covers the vacuum window and at the downstream side of which, the monitoring apparatus is disposed; and
an irradiation management apparatus that controls irradiation of the charged particle beam,
wherein a length of the low-scattering gas filling chamber is adjustable in such a manner that the monitoring apparatus is moveable in the beam-axis-direction relative to the vacuum window, and
wherein when the charged particle beam is irradiated, the low-scattering gas filling chamber is filled with a low-scattering gas that scatters the charged particle beam less than air does.

2. The particle beam irradiation apparatus according to claim 1,
wherein the low-scattering gas filling chamber includes the monitoring apparatus disposed at the downstream side thereof, a monitor holder that holds the monitoring apparatus, an upper seal disposed on the outer circumference of the vacuum duct, and a bellows that movably connects the upper seal with the monitor holder, and
wherein the monitoring apparatus is a cover of the downstream side in the low-scattering gas filling chamber.

3. The particle beam irradiation apparatus according to claim 1, wherein the monitoring apparatus includes a window plate so as to prevent the low-scattering gas from going downstream through the monitoring apparatus.

4. The particle beam irradiation apparatus according to claim 1, further including a low-scattering gas apparatus that supplies the low-scattering gas to and exhausts the low-scattering gas from the low-scattering gas filling chamber, wherein the low-scattering gas apparatus includes a gas supply unit that supplies the low-scattering gas to the low-scattering gas filling chamber, a volume fluctuation absorption unit that changes its volume in accordance with a fluctuation in the gas pressure of the low-scattering gas filling chamber, and a gas exhaust unit that exhausts the low-scattering gas from the low-scattering gas filling chamber.

5. The particle beam irradiation apparatus according to claim 4, wherein the gas exhaust unit includes an oil container containing an oil and a pipeline that connects the low-scattering gas filling chamber with the oil container.

6. The particle beam irradiation apparatus according to claim 4, wherein the gas exhaust unit includes a pipeline that exhausts the low-scattering gas from the low-scattering gas filling chamber to the downstream side of the monitoring apparatus.

7. The particle beam irradiation apparatus according to claim 1, further including a beam data processing apparatus that determines the beam size, based on passing position information of the charged particle beam detected by the position monitor, wherein the beam data processing apparatus includes a beam size calculation unit that calculates the beam size, based on the passing position information, and an abnormality determination unit that transmits an abnormality notification signal to the irradiation management apparatus when the difference between a planned desired beam size of the charged particle beam and the beam size calculated by the beam size calculation unit is not within the range of a determination threshold value.

8. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject, wherein the particle beam irradiation apparatus is according to claim 1.

9. The particle beam irradiation apparatus according to claim 2, wherein the monitoring apparatus includes a window plate so as to prevent the low-scattering gas from going downstream through the monitoring apparatus.

10. The particle beam irradiation apparatus according to claim 2, further including a low-scattering gas apparatus that supplies the low-scattering gas to and exhausts the low-scattering gas from the low-scattering gas filling chamber, wherein the low-scattering gas apparatus includes a gas supply unit that supplies the low-scattering gas to the low-scattering gas filling chamber, a volume fluctuation absorption unit that changes its volume in accordance with a fluctuation in the gas pressure of the low-scattering gas filling chamber, and a gas exhaust unit that exhausts the low-scattering gas from the low-scattering gas filling chamber.

11. The particle beam irradiation apparatus according to claim 3, further including a low-scattering gas apparatus that supplies the low-scattering gas to and exhausts the low-scattering gas from the low-scattering gas filling chamber, wherein the low-scattering gas apparatus includes a gas supply unit that supplies the low-scattering gas to the low-scattering gas filling chamber, a volume fluctuation absorption unit that changes its volume in accordance with a fluctuation in the gas pressure of the low-scattering gas filling chamber, and a gas exhaust unit that exhausts the low-scattering gas from the low-scattering gas filling chamber.

12. The particle beam irradiation apparatus according to claim 2, further including a beam data processing apparatus that determines the beam size, based on passing position information of the charged particle beam detected by the position monitor, wherein the beam data processing apparatus includes a beam size calculation unit that calculates the beam size, based on the passing position information, and an abnormality determination unit that transmits an abnormality notification signal to the irradiation management apparatus when the difference between a planned desired beam size of the charged particle beam and the beam size calculated by the beam size calculation unit is not within the range of a determination threshold value.

13. The particle beam irradiation apparatus according to claim 3, further including a beam data processing apparatus that determines the beam size, based on passing position information of the charged particle beam detected by the position monitor, wherein the beam data processing apparatus includes a beam size calculation unit that calculates the beam size, based on the passing position information, and an abnormality determination unit that transmits an abnormality notification signal to the irradiation management apparatus when the difference between a planned desired beam size of the charged particle beam and the beam size calculated by the beam size calculation unit is not within the range of a determination threshold value.

14. The particle beam irradiation apparatus according to claim 4, further including a beam data processing apparatus that determines the beam size, based on passing position information of the charged particle beam detected by the position monitor, wherein the beam data processing apparatus includes a beam size calculation unit that calculates the beam size, based on the passing position information, and an abnormality determination unit that transmits an abnormality notification signal to the irradiation management apparatus when the difference between a planned desired beam size of the charged particle beam and the beam size calculated by the beam size calculation unit is not within the range of a determination threshold value.

15. The particle beam irradiation apparatus according to claim 5, further including a beam data processing apparatus that determines the beam size, based on passing position information of the charged particle beam detected by the position monitor, wherein the beam data processing apparatus includes a beam size calculation unit that calculates the beam size, based on the passing position information, and an abnormality determination unit that transmits an abnormality notification signal to the irradiation management apparatus when the difference between a planned desired beam size of the charged particle beam and the beam size calculated by the beam size calculation unit is not within the range of a determination threshold value.

16. The particle beam irradiation apparatus according to claim 6, further including a beam data processing apparatus that determines the beam size, based on passing position information of the charged particle beam detected by the position monitor, wherein the beam data processing apparatus includes a beam size calculation unit that calculates the beam size, based on the passing position information, and an abnormality determination unit that transmits an abnormality notification signal to the irradiation management apparatus when the difference between a planned desired beam size of the charged particle beam and the beam size calculated by the beam size calculation unit is not within the range of a determination threshold value.

17. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject, wherein the particle beam irradiation apparatus is according to claim 2.

18. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject, wherein the particle beam irradiation apparatus is according to claim 3.

19. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject, wherein the particle beam irradiation apparatus is according to claim 4.

20. A particle beam therapy system comprising:
a beam generation apparatus that generates a charged particle beam and accelerates the charged particle beam by means of an accelerator;
a beam transport system that transports the charged particle beam accelerated by the accelerator; and
a particle beam irradiation apparatus that irradiates the charged particle beam transported by the beam transport system onto an irradiation subject, wherein the particle beam irradiation apparatus is according to claim 5.

* * * * *